United States Patent [19]

Boros et al.

[11] 4,110,415

[45] Aug. 29, 1978

[54] METHYLOL PHOSPHONATES AND PROCESS FOR MAKING SAME

[75] Inventors: Eugene Joseph Boros, South Charleston; Anthony Joseph Papa, Saint Albans, both of W. Va.

[73] Assignee: Union Carbide Corporation, New York, N.Y.

[21] Appl. No.: 645,133

[22] Filed: Dec. 29, 1975

[51] Int. Cl.$^2$ ............................ C07F 9/40; C08J 9/00
[52] U.S. Cl. .................................. 260/953; 260/969; 521/168; 521/180; 528/158
[58] Field of Search ................................ 260/969, 953

[56] References Cited

U.S. PATENT DOCUMENTS

| | | | |
|---|---|---|---|
| 3,189,635 | 6/1965 | Tieman | 260/941 |
| 3,332,893 | 7/1967 | Birum et al. | 260/953 X |

OTHER PUBLICATIONS

Kirby et al., "The Organic Chemistry of Phosphorus", Elsevier Publishing Co., New York, (1967), pp. 54–63.
Hudson, "Structure and Mechanism in Organophosphorus Chemistry", Academic Press, New York, (1965), pp. 177–182.
Abramov, "Chem. Abstr.", vol. 49, 6084e (1955).
Ginsburg et al., "Zh. Obsh. Khim.", 30, 3979 (1960).
Ramirez et al., "J. Am. Chem. Soc.", vol. 86, 514, 1964.

*Primary Examiner*—Anton H. Sutto
*Attorney, Agent, or Firm*—Reynold J. Finnegan

[57] ABSTRACT

Novel polymethylol polyphosphonates are prepared by reacting a trisubstituted polyphosphite having at least one alkyl group and formaldehyde. The phosphite reactant may contain the requisite hydroxyl functionality [e.g. - heptakis (dipropylene glycol) triphosphite] or the hydroxyl functionality may be introduced by carrying out the reaction in the presence of a polyol, e.g. - glycerol, as a protic solvent. The resulting reaction product is a water-soluble liquid of relatively low viscosity and may be employed without any refining. The thus-formed polyphosphonates can be readily incorporated into either rigid urethane foam formulations to impart flame retardancy or phenolic resins to improve flexibility.

10 Claims, No Drawings

METHYLOL PHOSPHONATES AND PROCESS FOR MAKING SAME

BACKGROUND OF THE INVENTION

This invention relates to novel organophosphorus compounds and, more particularly, to novel polymethylol polyphosphonates capable of imparting adeqate flame retardancy to rigid polyurethane foams and providing flexibility when used as modifiers for phenolic resins.

Hydroxyl-containing phosphonate derivatives are commercially available, one example being diethyl N,N-bis (2-hydroxyethyl) aminomethylphosphonate. Such materials are typically used to impart flame retardancy to cotton fabrics, polyurethane foams or the like. In addition to possessing flame retardancy, phosphorous derivatives of the polyphosphonate type possess the advantage of exhibiting outstanding hydrolytic stability.

However, the commercially available materials generally tend to be relatively low in both hydroxyl and phosphonate functionality; and it would be desirable to provide phosphonates in which both types of functionality were increased. Increasing hydroxyl functionality will improve the ability of the compounds to be compatibly and chemically incorporated into the rigid polyurethanes being formed. Also, the incorporation of lower hydroxyl functionality materials does tend to adversely effect the properties of rigid polyurethane foams. Incorporation of increasing amounts of phosphonate functionality should provide improved flame retardancy properties since the presence of phosphorus in this functionality is generally accepted as the most desirable insofar as flame retardancy is concerned. Still further, the commercially available phosphonates are relatively expensive; and a facile, inexpensive synthesis for phosphonates having relatively high hydroxyl and phosphonate functionalities would be desirable.

The reaction of trialkyl phosphites with aliphatic aldehydes to form phosphonates have been reported in the literature, typically designated as Arbuzov reactions. In the absence of solvents, the reaction has been reported as occurring according to the following equation:

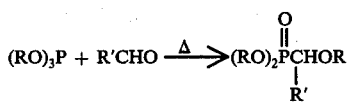

In the presence of a protic solvent, it is reported that the reaction proceeds thusly:

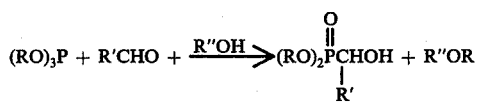

Still further, at low temperatures and under anhydrous conditions, the reaction has been reported to follow the equation hereinafter set forth:

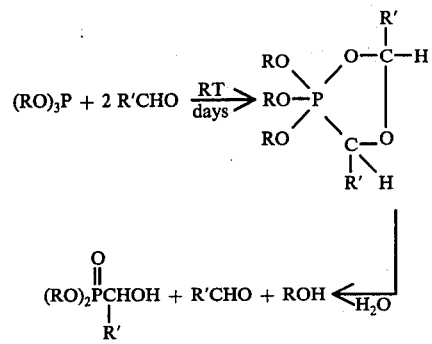

Such reactions have typically been employed using relatively low moleclar weight trialkylphosphites. Moreover, it is believed that Arbuzov reactions have not used formaldehyde as the aldehyde reactant.

It is an object of the present invention to provide novel polymethylol polyphosphonates possessing relatively high hydroxyl and phosphonate functionalities. A related and more specific object provides phosphonates which are capable of imparting adequate flame retardancy to polyurethane materials such as rigid polyurethane foams and flexibility to phenolic resins.

Another and more specific object provides a method for readily converting hydrolytically unstable phosphites to hydrolytically stable and useful polyphosphonates.

Yet another object lies in the provision of an economically attractive, facile process for synthesizing such polyphosphonates. A related and more specific object of this invention is to provide a process in which the reaction products may be used without the necessity of any further refining.

Other objects and advantages of the present invention will become apparent from the following detailed description.

While the invention is susceptible to various modifications and alternative forms, there will herein be described in detail the preferred embodiments. It is to be understood, however, that it is not intended to limit the invention to the specific forms disclosed. On the contrary, it is intended to cover all modifications and alternative forms falling within the spirit and scope of the invention as expressed in the appended claims.

SUMMARY OF THE INVENTION

In general, the present invention is predicated on the discovery that unique polymethylol polyphosphonates can be prepared by reacting particular trisubstituted phosphites having at least one alkyl group with formaldehyde. In accordance with one aspect of the present invention, the phosphite reactant consists of a polyphosphite containing the requisite hydroxyl functionality; and, in another aspect, when the phosphite reactant does not contain hydroxyl functionality, a protic solvent employed provides the necessary polyol functionality, e.g. - certain low moleclar weight polyols are utilized. The novel polymers formed are water-soluble liquids of relatively low viscosity characterized by the following functional group:

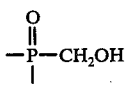

Such polymethylol polyphosphonates can be readily incorporated into either rigid urethane foam formulations to impart flame retardancy or phenolic resins to improve flexibility.

DETAILED DESCRIPTION OF THE INVENTION AND PREFERRED EMBODIMENTS

In accordance with one aspect of the present invention the phosphite reactant comprises a species containing two or more hydroxyl groups. Suitable species inclde heptakis (dipropylene glycol) triphosphite:

wherein

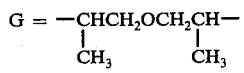

and tris(dipropylene glycol) phosphite:

(HOGO)$_3$P where G is defined as above. Utilization of such polyhydroxy-containing reactants avoids the necessity of using a protic solvent and will generally result in avoiding the need for any refining of the reaction product. These species are commercially available.

In accordance with a further aspect of the present invention, polyphosphites which do not contain the required hydroxyl groups as part of the reactant may also be used. The following polyphosphites may thus be employed: diisodecyl pentaerythritol diphosphite, distearyl pentaerythritol diphosphite, bis (neopentylglycol) 1,4-cyclohexanedimethylene phosphite, dineodecyl pentaerythritol diphosphite, bis neopentylglycol triethyleneglycil diphosphite, diphenylpentaerythritol diphosphite, tetra (diphenylphosphite) pentaerythritol and tetrakis (nonylphenyl) polypropyleneglycol diphosphite (the polypropyleneglycol moiety having an average molecular weight of about 425). All of these polyphosphites are commercially available. In addition, polyphosphites containing the following repeating units may be employed:

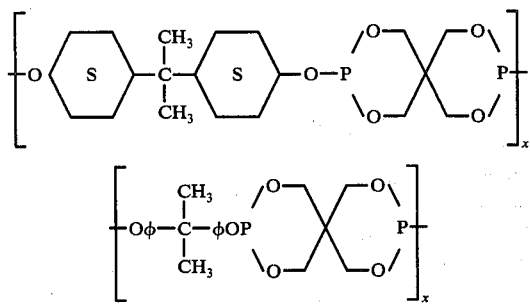

These are commercially available from Weston Chemical Company and are identified, respectively, as "Weston 422 Phosphite" and "Weston 1621 Phosphite". The former is a clear glassy solid having a melting point of about 35° C. (minimum) and contains about 13.7–14.8 percent phosphorus and a maximum of about 9.0 percent phenoxy groups. The latter is also a clear glassy solid, has a melting point of about 50° C. (minimum) and contains about 15.0–16.6 percent phosphorus and a maximum of about 9.0 percent phenoxy groups. Further description of these materials is set forth in U.S. Pat. No. 3,053,878. The use of these non-hydroxyl containing polyphosphites requires special processing, as will be described hereinafter, to introduce the necessary polyol functionality to form the novel polymethylol polyphosphonates of the present invention.

As should be appreciated, the present invention is not limited to the particular polyphosphite reactants described herein. Conceptually, any trisubstituted polyphosphite having at least one alkyl group may be employed. The species identified herein are however preferred due to their commercial availability.

To form the novel compounds of the present invention, the polyphosphite reactant is reacted with formaldehyde, conveniently in the form of paraformaldehyde, at ambient conditions in the presence of a polyhydroxy protic solvent hen the polyphosphite reactant does not contain the necessary hydroxyl functionality. The reaction is mildly exothermic and may be suitably carried out in a stirred vessel at temperatures varying in the range of from about 25° to 110° C., or a somewhat higher temperature if desired.

The protic solvent utilized when the polyphosphite reactant does not contain the necessary hydroxyl functionality may be any polyol. Desirably, any of the several known and commercially available low molecular weight polyols may be employed as the protic solvent in this instance. For example, glycerol; 1,2,6-hexanetriol; ethylene glycol; diethylene glycol; tetraethylene glycol; propylene glycol; dipropylene glycol; tetrapropylene glycol; trimethylol propane; trimethyolethane; 1,2-, 1,3- and 1,4-butylene glycols; 1,5-pentanediol; and the like, including mixtures thereof, may be employed. In addition, higher molecular weight polyols, amines and mercaptans may be utilized. Suitable polyols are set forth hereinafter in connection with the description of suitable reactants for the urethane foam formulations.

While, conceptually, any polyol may be employed, it should be appreciated that viscosity and physical state considerations should be kept in mind. It is thus preferred to utilize polyols that are liquid and have a viscosity which allows ease of handling. Indeed, while the polyol need not be a liquid at ambient temperatures, it should be a liquid at the reaction temperature used.

The relative amounts of the reactants can be varied within wide limits. To achieve complete reaction, the formaldehyde should be present in at least a stoichiometric amount. As can be seen from the Examples, the stoichiometry needed is the ratio of the moles of formaldehyde to the phosphorus atoms present, which ratio is desirably between 1 and 2/1. Utilizing the formaldehyde/polyphosphite ratios set forth herein will provide the desired HCHO/P atom ratio. The mole ratio of the formaldehyde/polyphosphite reactant may accordingly desirably vary from about 1 to 6 to 1, or even higher, if desired. It is not preferred to utilize large excesses of formaldehyde as this may make refining to remove the excess desirable or even necessary. Similarly, when employed, the protic solvent can likewise be present in varying amounts. The protic solvent should be present in at least a stoichiometric amount so that the necessary hydroxyl functionality is introduced. However, if a solvent is desirable for any reason, amounts in excess of the stoichiometric amount may be utilized. As with the formaldehyde, large excesses are not preferred.

In general, the novel polyphosphonate reaction product may be characterized by the following functional groups:

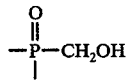

A single structure cannot adequately describe the reaction product as a broad distribution of molecular species are believed to result. The average molecular weight of the reaction product will vary, principally depending upon the particular polyphosphite reactant which was employed.

The products of the present invention are typically clear, nearly colorless liquids of low viscosity which are soluble in water. And, in contrast to the phosphite reactants which may be employed, the resulting products are not readily hydrolyzed. While unnecessary, the crude reaction product may be refined by any conventional means, if desired, typically to remove volatile matter (e.g. - unreacted alcohols and low boiling (phosphonates).

The novel products of the present invention may be utilized as flame retardant or low combstibility additives in connection with rigid polyurethane foams. The polyurethane foams may be prepared by reacting and forming, as is known: (a) a polyol, (b) an organic polyisocyanate, (c) a catalyst for the reaction of (a) and (b) to produce the polyurethane, (d) a blowing agent and (e) a foam stabilizer. The reaction and foaming operations can be performed in any suitable manner, preferably by the one-shot technique.

The polyol will have an average of at least 2 and usually not more than 8 active hydrogen atoms present as hydroxyl groups. Such organic polyol reactants include compounds consisting of carbon, hydrogen and oxygen as well as compounds which contain these elements in combination with other elements such as phosphorous, halogen and/or nitrogen. Suitable classes of organic polyol reactants for use in this invention are polyetherpolyols, polyesterpolyols, polylactonepolyols, nitrogen-containing polyols, phosphorous-containing polyols and phenolic-based polyols.

It is well known to the polyurethane art that the particular polyol reactant or combination of polyols employed depends upon the end-use of the polyurethane product which in turn determines whether the product is to be provided as a flexible, semi-flexible or rigid material. For this purpose, the polyol reactant is usually characterized by its hydroxyl number which is determined by and defined as the number of milligrams of potassium hydroxide required for the complete neutralization of the hydrolysis product of the fully acetylated derivative prepared from 1 gram of polyol or mixture of polyols. The hydroxyl number is also defined by the following equation which reflects its relationship with the functionality and molecularweight of the polyol reactant:

$$OH = (56.1 \times 1000 \times f/M.W.)$$

wherein OH = hydroxyl number of the polyol;
$f$ = average functionality, that is, average number of hydroxyl groups per molecule of polyol; and
M. W. = average molecular weight of the polyol. The polyols may have hydroxyl numbers ranging from about 20 to about 1000. In producing flexible foams, polyols having relatively low hydroxyl numbers such as from about 20 to about 100 are generally employed. In producing semi-flexible materials, the hydroxyl number is usually from about 100 to about 300. Polyols having reltively high hydroxyl number of from about 300 to about 1000 are used in rigid foam formulations.

Suitable polyethers that can be employed include linear and branched polyethers preferably having a plurality of ether linkages and containing at least two hydroxyl groups and being substantially free from functional groups other than hydroxyl. These compounds include alkylene oxide adducts of water such as polyethylene glycols having average molecular weights from about 200 to about 600, polypropylene glycols having average molecular weights from about 400 to about 2000, and polyoxyalkylene polyols having a combination of different alkylene oxide units. Other suitable polyols encompassed are the alkylene oxide adducts of polyhydric organic initiators, the nature of which determines the average hydroxyl functionality of the polyoxyalkylated product. Illustrative of suitable polyhydric organic initiators are the following which can be employed individually or in combination with one another: (1) diols such as ethylene glycol, diethylene glycol, propylene glycol, 1, 5-pentanediol, hexylene glycol, dipropylene glycol, trimethylene glycol, 1, 2-cyclohexanediol, 3-cyclohexene-1, 1-dimethanol and 3, 4-dibromocyclohexane-1, 1-dimethanol; (2) triols such as glycerol, 1, 2, 6-hexanetriol, 1, 1, 1-trimethylolethane, 1, 1, 1-trimethylolpropane, 3-(2-hydroxyethoxy)- and 3-(2-hydroxypropoxy)-1, 2-propanediols, 2, 4-dimethyl-2-(2-hydroxyethoxy) methyl-pentanediol-1, 5, 1, 1, 1-tris [(2-hydroxyethoxy) methyl] ethane and 1, 1, 1-tris[(2-hydroxypropoxy) methyl] propane; (3) tetrols such as pentaerythritol; (4) pentols, hexols, heptanols and octanols such as glucose, sorbitol, bis(2, 2, 4-tri-methylol) ethylether, alpha-methyl glucoside, sucrose, mannose and galactose; (5) compounds in which hydroxyl groups are bonded to an aromatic nucleus such as resorcinol, pyrogallol, phloroglucinol, di-, tri- and tetraphenylol such as bis(p-hydroxyphenyl) methane and 2, 2-bis(p-hydroxyphenyl)-propane; and (6) alkylene oxide adducts of the aforesaid initiators such as propylene or ethylene oxide adducts of glycerol having a relatively low average molecular weight up to about 650. Particularly useful in the preparation of flexible foams generally are polyether polyols having an average hydroxyl functionality of from about 2.1 to about 4. Such polyols are provided by the employment of either trihydric or tetrahydric starters, mixtures thereof, or appropriate mixtures containing diol starters. The more highly functional polyether polyols are usually employed in providing the semi-flexible and rigid foams.

The above-described polyether polyols are normally liquid materials and, in general, are prepared in accordance with well known techniques comprising the reaction of the polyhydric starter and an alkylene oxide in the presence of an oxyalkylation catalyst. Usually, the catalyst is an alkali metal hydroxide such as, in particular, potassium hydroxide. The oxyalkylation of the polyhydric initiator is carried out at temperatures ranging from about 90° C. to about 150° C. and usually at an elevated pressure up to about 200 p.s.i.g., employing a sufficient amount of alkylene oxide and adequate reaction time to obtain a polyol of desired molecular weight which is conveniently followed during the course of the reaction by standard hydroxyl number determinations, as defined above. The alkylene oxides most commonly employed are the lower alkylene oxides, that is, compounds having from 2 to 4 carbon atoms including ethylene oxide, propylene oxide, butylene oxides (1, 2- or 2, 3-) and combinations thereof. When more than one type of oxyalkylene unit is desired in the polyol product, the alkylene oxide reactants may be fed to the reaction system sequentially to provide polyoxyalkylene chains containing respective blocks of different oxyalkylene units or they may be fed simultaneously to provide substantially random distribution of units. Alternatively, the polyoxyalkylene chains may consist essentially of one type of oxyalkylene unit such as oxypropylene capped with oxyethylene units.

Other types of suitable polyol reactants for use in producing cellular polyurethanes as described herein are polyester polyols containing an average of at least two hydroxyl groups per molecule (as alcoholic OH or as OH in -COOH groups). As is known to the art such polyester polyols are provided as the reaction products of: (1) a polyfunctional organic carboxylic acid, and (2) one or more of the aforesaid polyether polyols, or one or more of the aforesaid polyhydric organic initiators which are reacted with alkylene oxide to product such polyether polyols, such as, for example, diethylene glycol, glycerol and 1, 1, 1-trimethylolpropane. Among the suitable polycarboxylic acids that can be employed in producing such polyester polyols are: the aliphatic acids which are usually free of reactive unsaturation such as ethylenic and acetylenic groups, such as, for example, succinic, adipic, sebacic, azelaic, glutaric, pimelic, malonic and suberic acids; cycloaliphatic acids such as chlorendic acid; and aromatic polybasic acids such as phthalic, terephthalic, isophthalic acids and the like. Other polycarboxylic acids that can be employed are the "dimer acids" such as the dimer of linoleic acid. Hydroxyl-containing monocarboxylic acids (such as ricinoleic acid) can also be used. Alternatively, the anhydrides of any of these various acids can be employed in producing the polyester polyols.

Also contemplated for use as a polyol reactant of the foam formulations employed in the practice of this invention are nitrogen-containing polyols. Such polyols include lower alkylene oxide adducts of the following amines which may be employed individually or in combination: primary and secondary polyamines such as ethylenediamine, diethylenetriamine and toluenediamine; and aminoalkanols such as ethanolamine, diethanolamine, triethanolamine and triisopropanolamine. Also suitable are mixed starters containing one or more of the aforesaid polyfunctional amines, aniline, and/or one or more of the polyhydric initiators employed to produce Polyol I such as dipropylene glycol, glycerol and sucrose. Also illustrative of suitable nitrogen-containing polyols are aniline/formaldehyde and aniline/phenol/formaldehyde condensation products. Such amine-based polyols are usually employed in rigid foam formulations.

Other suitable polyols for use in producing polyurethane foams as described herein are: lactone-based polyols prepared by reacting a lactone such as epsilon-caprolactone, or a mixture of epsilon-caprolactone and an alkylene oxide, with a polyfunctional initiator such as a polyhydric alcohol, an amine, or an aminoalcohol; phosphorus-containing polyols such as the alkylene oxide adducts of phosphoric acid, polyphosphoric acids such as tri- and tetra-phosphoric acids, organo-substituted phosphoric acids such as benzenephosphoric acid; and other polyol reactants known to the polyurethane art.

The organic polyisocyanates that are useful in producing polyurethane foams in accordance with this invention are organic compounds that contain at least two isocyanato groups. Such compounds are well known in the art of producing polyurethane foams. Suitable organic polyisocyanates include the hydrocarbon diisocyanates, (e.g., the alkylene diisocyanates and the arylene diisocyanates) as well as known triisocyanates. As examples of suitable polyisocyanates one can mention 1, 2-diisocyanatoethane, 1, 3-diisocyanatopropne, 1, 2-diisocyanatopropane, 1, 4-diisocyanatobutane, 1, 5- diisocyanatopentane, 1, 6-diisocyanatohexane, bis (3-isocyanatopropyl) ether, bis (3-isocyanatopropyl) sulfide, 1, 7-diisocyanatoheptane, 1, 5-diisocyanato-2, 2-dimethylpentane, 1, 6-diisocyanato-3-methoxyhexane, 1, 8-diisocyanato-octane, 1, 5-diisocyanato-2, 2, 4-trimethylpentane, 1, 9-diisocyanatononane, 1, 10-diisocyanatopropyl) ether of 1, 4-butylene glycol, 1, 11-diisocyanatoundecane, 1, 12-diisocyanatododecane bis (isocyanatohexyl) silfide, 1, 4-diisocyanatobenzene, 2, 4-diisocyanatotoluene, 2, 6-diisocyanato tolyene, 1, 3-diisocyanato-o-xylene, 1, 3-diisocyanato-m-xylene, 1, 3-diisocyanato-p-xylene, 2, 4-diisocyanato-1-chlorobenzene, 2, 4-diisocyanato-1-nitrobenzene, and 2, 5-diisocyanato-1-nitrobenzene and mixtures thereof.

The catalyst that are useful in producing polyurethane foams in accordance with this invention include: (a) tertiary amines such as bis (dimethylamino ethyl) ether, trimethylamine, triethylamine, N-methylmorpholine, N-ethylmorpholine, N, N-dimethylbenzylamine, N, N-dimethylethanolamine, N, N, N', N'-tetramethyl-1, 3-butanediamine, triethanolamine, 1, 4-diazabicyclo[2.2.2]octane, pyridine oxide and the like; (b) tertiary phosphines such as trialkylphosphines, dialkylbenzylphosphines, and the like; (c) strong bases such as alkali and alkaline earth metal hydroxides, alkoxides, and phenoxides; (d) acidic metal salts of strong acids such as ferric chloride, stannic chloride, stannous chloride, antimony trichloride, bismuth nitrate and chloride, and the like; (e) chelates of varous metals such as those which can be obtained from acetylacetone, benzoylacetone, trifluoroacetylacetone, ethyl acetoacetate, salicylaldehyde, cyclopentanone-2-carboxylate, acetylacetone-imine, bisacetylacetonealkylene-diimines, salicylaldehydeimine, and the like, with various metals such as Be, Mg, Zn, Cd, Pb, Ti, Zr, Sn, As, Bi, Cr, Mo, Mn, Fe, Co, Ni, or such ions as $MoO_2++$, $UO_2++$, and the like; (f) alcoholates and phenolates of various metals such as $Ti(OR)_4$, $Sn(OR)_4$, $Sn(OR)_2$, $Al(OR)_3$, and the like, wherein R is alkyl or aryl, and the reaction products of alcoholates with carboxylic acids, betadiketones, and 2-(N, N-dialkylamino) alkanols, such as the well known chelates of titanium obtained by said or equivalent procedures; (g) salts of organic acids with a variety of metals such as alkali metals, alkaline earth metals, Al, Sn, Pb, Mn, Co, Ni, and Cu, including, for example, sodium acetate, potassium laurate, calcium hexanoate, stannous acetate, stannous octoate, stannous oleate, lead octoate, metallic driers such as manganese and cobalt naphthenate, and the like; (h) organometallic derivatives of tetravalent tin, trivalent and pentavalent As, Sb, and Bi, and metal carbonyls or iron and cobalt.

Among the organotin compounds that deserve particular mention are dialkyltin salts of carboxylic acids, e.g. dibutyltin diacetate, dibutyltin dilaurate, dibutyltin maleate, dilauryltin diacetate, dioctyltin diacetate, dibutyltin-bis (4-methylaminobenzoate), dibutyltinbis (6-methylaminocaproate), and the like. Similarly there may be used a trialkyltin hydroxide, dialkyltin oxide, dialkyltin dialkoxide, or dialkyltin dichloride. Examples of these compounds include trimethyltin hydroxide, tributyltin hydroxide, trioctyltin hydroxide, dibutyltin oxide, dioctyltin oxide, dilauryltin oxide, dibutyltin-bis (isopropoxide), dibutyltinbis (2-dimethylaminopentylate), dibutyltin dichloride, dioctyltin dichloride, and the like.

The tertiary amines may be used as primary catalysts for accelerating the reactive hydrogen/isocyanate reaction or as secondary catalysts in combination with one or more of the above noted metal catalysts. Metal catalysts, or combinations of metal catalysts, may also be employed as the accelerating agents, without the use of amines. The catalysts are employed in small amounts, for example, from about 0.001 per cent to about 5 per cent, based on weight of the reaction mixture.

Foaming is accomplished by employing a small amount of a polyurethane blowing agent, such as water, in the reaction mixture (for example, from about 0.5 to about 5 weight per cent of water), or through the use of blowing agents which are vaporized by the exotherm of the reaction, or by a combination of the two methods. Illustrative polyurethane blowing agents include halogenated hydrocarbons such as trichloromonofluoromethane, dichlorodifluoromethane, dichloromonoflurormethane, dichloromethane, tri chlormethane, 1, 1-dichloro-1-fluoroethane, 1, 1, 2-trichloro-1, 2, 2-trifluoromethane, hexafluorocyclobutane, octafluorocyclobutane, and the like. Another class of blowing agents include thermally-unstable compounds which liberate gases upon heating, such as N, N'-dimethyl-N, N'-dinitrosoterephthalamide, and the like. The generaly preferred method of foaming for producing flexible foams is the use of water or a combination of water plus a fluorocarbon blowing agent such as trichloromonofluoromethane. The quantity of blowing agent employed will vary with factors such as the density desired in the foamed product.

In producing cellular polyurethanes in accordance with the method of this invention, a minor amount of an organosilicone or a silicone-free, organic surfactant may also be present as an additional component of the polyurethane-forming reaction mixture, organosilicone surfactants being preferred. Whe used, such surfactants are usually present in amounts up to about 5 parts by weight per 100 parts by weight of total polyol reactant.

Suitable classes of silicone surfactants are the polysiloxanepolyoxyalkylene block copolymers wherein the respective blocks are joined through silicon-to-carbon or silicon-to-oxygen-to-carbon bonds and the respective polyoxyalkylene blocks are bonded to different silicon atoms of the polysiloxane backbone to form a comb-like structure. Usually, the polysiloxane blocks are trialkylsiloxy-endblocked. In addition to the siloxy units to which the pendant polyoxyalkylene chains are bonded, the polysiloxane backbone is formed of difunctional siloxy units wherein the respective two remaining valences of silicon are satisfied by bonds to organic radicals. Illustrative of such organic radicals are the hydrocarbyl groups having from 1 to 12 carbon atoms including alkyl, aryl, aralkyl, bicycloheptyl and halogen-substituted derivatives of such groups. The polyalkylene blocks are usually constituted of oxyethylene units, oxypropylene units or a combination of such units, and the polyoxyalkylene chains are hydroxyl-terminated or capped with a monovalent orgaic group such as alkyl, aryl, aralkyl, acyl, carbamyl and the like.

A second type of foam-stabilizing component which can be present in the formulations described herein are the branched block copolymers described in U.S. Pat. No. 2,834,748. Organosilicone foam stabilizer described in the latter patent include those containing a trifunctional siloxy unit to which three polyoxyalkylene blocks are bonded through dialkyl-substituted siloxy units. A preferred group are those having the formula, $MeSi[OSiMe_2)_d(OC_aH_{2a})_bOR]_3$, wherein Me is methyl, $d$ has a value of at least one, $a$ is from 2 to 3, $b$ has a value of at least 5, and R is hydrogen or a monovalent hydrocarbyl group such as lower alkyl, butyl being especially suitable.

Other useful foam-stabilizing components are bock copolymers wherein the polysiloxane blocks are trialkylsiloxy-endblocked and contain recurring difunctional dialkylsiloxy monomeric units in combination with reoccurring difunctional cyanoalkyl-alkylsiloxy or cyanoalkoxy-alkylsiloxy monomeric units, the mole ratio of the dialkylsiloxy units to the cyano-substituted siloxy units being about 10-200: 3-100, and wherein the polysiloxane and polyoxyalkylene blocks are joined through an Si-C or an Si-O-C linkage, and from about 20 to about 65 weight percent of the oxyalkylene content of the polyoxyalkylene blocks is constituted of oxyethylene units. These block copolymers are described and claimed in copending application Ser. No. 279,883, filed Aug. 11, 1972, in the name of Bela Prokai and Bernard Kanner. A preferred class of such surfactants are the cyanopropyl-substituted block copolymers having the average formula,

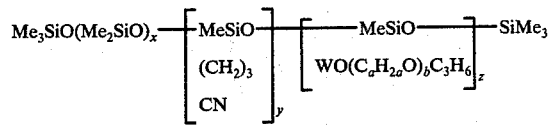

wherein: Me represents methyl; W represents a monovalent hydrocarbyl group (R'—), an acyl group [R'C(O)—] or a carbamyl group [R'NHC (O)—], the said R' group having from 1 to 12 carbon atoms; $x$ has an average value of from about 20 to about 100; $y$ has an average value of from about 4 to about 30; $z$ has an average value of from about 2 to about 10; $a$ has a value of from 2 to 4, provided from about 20 to about 65 weight percent of the oxyalkylene units of the polyoxyalkylene chain, $—(C_aH_{2a}O)_b—$, are constituted of oxyethylene; and $b$ has an average value such that the average molecular weight of the polyoxyalkylene chain is from about 1000 to about 6000.

Still further suitable silicon-containing foam stabilizers include the polysiloxane-polyoxyalkylene block copolymers described, for example, in U.S. Pat. Nos.

3,563,924 and 3,594,334. Such copolymers include those characterized by a particular molecular weight (600-17000), siloxane content (14-40 weight percent based on the weight of the copolymer) and oxyethylene content (at least 75 weight percent based on the total amount of oxyalkylene groups in he copolymer). The organosilicones are usually employed in combination with an anionic, silicon-free organic emulsifier such as those described in said U.S. Pat. No. 3,594,334, the teachings of which are incorporated herein by reference. Also effective as stabilizers are the organosilicones containing tetrafunctional $SiO_{4/2}$ units described and claimed in copending application Ser. No. 132,534, filed Apr. 8, 1971, in the names of Bela Prokai and Bernard Kanner. Of this class of stabilizers, those having the following average formula are particularly preferred:

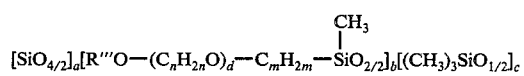

wherein $n$ has a value of 2 to 4 inclusive; $d$ has an average value of from about 5 to about 15; m has a value of from 2 to 4; a:b:c has an average value of 0.4-2:1:0.2-2, and R''' is phenyl, lower alkyl, lower alkaryl or aryl-substituted lower akyl groups. Particularly effective are polymers in which at least a major proportion of the poly (oxyalkylene) chains are terminated by R°°°O- groups where the orgaic cap (R°°°) is methyl or benzyl.

Still further useful silicone surfactants include cyanopropyl-substitued polymethylsiloxane-polyoxyethylene copolymers described in copending application Ser. No. 457,510, filed Apr. 3,1974, of Bela Prokai and Bernard Kanner. Other useful silicone surfactants comprise the cyanoalkoxyalkyl-modified polyalkylsiloxane-polyoxyethylene copolymers described in copending application Ser. No. 536,884, filed Dec. 27, 1974, of Bela Prokai and Bernard Kanner.

Silicon-free, organic surfactants or emulsifiers suitable as stabilizers of the polyester polyol-based urethane foams described herein are known to the art and are employed in amounts up to about 5 p.p.h.p. One class of orgaic emulsifiers suitable for this purpose are products obtained by the reaction of amines such as, in particular, diethylamine, with long chain fatty acids such as oleic acid or with sulfonated $C_{10}$-$C_{15}$ alkylated aromatic hydrocarbons. Another class are the liquid, anionic organic surfactants having at least one carbon-bonded sulfonic acid group, —$SO_3H$, or an ammonium, quaternary ammonium, alkali metal or alkaline earth metal derivative of said sulfonic acid group. The sulfonic acid groups or salt derivative thereof can be substituents on a wide variety of "backbone" organic compounds which provide the hydrophobic portion of the emulsifier. The hydrophobic portion may consist of carbon and hydrogen as in sulfonated hydrocarbons (or salt derivatives thereof) having from 10 to 20 or more carbon atoms such as alkanes, high alkyl-substituted benzenes, and liquid petroleum fractions, as typically illustrated by sodium tetradecyl sulfonate, sodium dodecylbenzene sulfonate and sodium and potassium salts of sulfonated mineral oil. The —$SO_3H$ group or salt derivative thereof may also be a substituent on an organic backbone consisting of carbon, hydrogen and oxygen wherein oxygen is present in an ether linkage as in polyoxyalkylene groups or in a carboxylic acid ester group. Typical of such compounds are those obtained by sulfating or sulfonating oxyalkylated fatty acid esters wherein the oxyalkylation is usually effected with ethylene oxide, propylene oxide or a combination thereof. These and other organic stabilizers of polyester polyol-derived urethane foams are known to the art; see, for example, the description thereof in U.S. Pat. No. 3,954,334.

If desired, other additional ingredients can be employed in minor amounts in producing the polyurethane foams in accordance with the process of this invention. Illustrative of such additives that can be employed are: compression set additives (e.g., hexylene glycol); additives to regulate cell structure so as to coarsen cells and thereby reduce the tendency of the foam to split (e.g., paraffin oil); fillers; dyes; pigments; antidiscoloration additives including anti-scorch and anti-oxidation agents; and the like.

While the novel reaction products of this invention could conceivably be used with flexible foam formulations, such use will generally be undesirable due to the relatively high hydroxyl functionality of the products and processing problems which will be associated. The urethane reactants should accordingly be selected to provide at least a semi-flexible foam and, preferably, a rigid foam.

The novel polymethylol phosphonates of the present invention may be compounded with the foam formulation being employed by any of the conventional techniques used for flame retardant additives. The amount used may be varied within wide limits; and as little as from about 5 to 10 parts by weight of the novel polymethylol polyphosphonates per 100 parts of the polyol constituent provide the resulting foams with satisfactory flame retardance. Amounts up to about 20 parts or more may also suitably be employed.

It is further desirable to employ the polymethylol polyphosphonates of this invention as impact modifiers for phenolic resole resins to impart flexibility. And, still further, due to the phosphorousmethylol functionality, the polymethylol polyphosphonates may provide utility in connection with conventional aminoplast resins typically employed to couple organophosphorus flame retardant materials to cellulosic textiles, such as cotton.

The following Examples are illustrative, but not in limitation, of the present invention.

Definitions

As used in the Examples appearing hereinafter, the following designations, symbols, terms and abbreviations have the indicated meanings:

| TERMS | DEFINITIONS |
|---|---|
| Polyol | A propoxylated aromatic polyol resulting from the reaction of propylene oxide with a condensate of phenol/analine/formaldehyde having a hydroxyl number of about 375, an alkalinity of about 1.5 meg/g, and a molecular weight of about 500. |
| Surfactant A | A silicone surfactant used mainly for rigid foam stabilization having the following idealized structure: |

-continued

| TERMS | DEFINITIONS |
|---|---|
| Cream Time | $Me_3SiO(Me_2SiO)_{13}[HO(C_2H_4O)_{7.5}C_3H_6SiMeO]_{5.5}SiMe_3$<br>The interval of time from the formation of the complete foam formulation to the appearance of a creamy color in the formulation. The creaming time is proportional to the rate of reaction of the formulation. |
| Gel Time | The observed elapse of time from the time the foaming mixture was poured into a container and stringing (gelation) of the polymer occurs as determined by intermittently protruding the top of the foam with a spatula. |
| Flame Retardant A | $$(C_2H_5O)_2\overset{O}{\overset{\|}{P}}-CH_2N(CH_2CH_2OH)_2;$$<br>a commercially available phosphonate polyol having a hydroxyl number of 440 (MgKOH/g) and a phosphorus content of 12.2% ("Fyrol 6", Stauffer Chemical Company). |
| Flame Retardant B | Heptakis (dipropylene glycol) triphosphite |
| Rise Time | The interval of time from the formation of the complete foam formulation to the attainment of the maximum height of the foam. |
| Free-Blow Density | Measured as described in Sections 68-73 of ASTM D 1632. |
| Closed Cells, percent | Measured in accordance with the procedures set forth in ASTM D 1940. |
| Compressive Strength | Determined using ASTM test method D 1621. |
| Flammability | Flammability ratings were obtained by measurements made in accordance with standard test procedure ASTM D 1692-67T. |
| Oxygen Index | ASTM 2863-70 |
| Surfactant B | A silicone surfactant used mainly for rigid urethane foam stabilization and having the following idealized structure:<br>$Me_3SiO(Me_2SiO)_{43.2}[MeO(C_3H_6O)_{5.8}(C_2H_4O)_{25}C_3H_6SiMeO]_{6.8}SiMe_3$ |
| Blowing Agent A | 1, 1, 2 Trichloro-1, 2, 2-trifluoroethane. |
| Friability Resistance | Measured using a combination of ASTM C 367 and C 421 tumbling test. The test specimens were conditioned in accordance with ASTM C 367, and the test time intervals were used as described by ASTM C 421. |
| Cold Aging | The foam samples were refrigerated at −30° C. for 14 days as described by ASTM D-2126B. |
| Dry Aging | The foam was heated in an oven at 70° C. at 5% relative humidity for 14 days as described by ASTM D-2126E. |
| Humid Aging | The foam specimen was heated at 70° C. for 28 days in a steam autoclave at 100% relative humidity in accordance with ASTM D-2126F. |
| Phenolic Resin | A liquid phenolic resole resin prepared by an alkaline catalyzed reaction of phenol and formaldehyde and having a viscosity of about 5000 cps. at 20° C. |
| Blowing Agent B | Trichlorofluoromethane |

EXAMPLES 1 – 8

Novel polymethylol polyphosphonates according to the present invention were made by reacting heptakis (dipropylene glycol) triphosphite and paraformaldehyde using various mole ratios for the reactants and varying reaction parameters.

In general, the procedure carried out was as follows. A mixture of the triphosphite reactant and the paraformaldehyde were placed in a 1-liter, 4-necked flask equipped with a Trubor stirrer, thermometer, nitrogen inlet and condenser. The flask was heated by means of a heating mantle; and, while stirring, nitrogen was passed over the mixture. The mixture was then heated slowly to a temperature at which an exotherm set in. The temperature was then held constant at the reaction temperature for the reaction time employed.

In Examples 1-5, the crude product was refined by passage through a Rota-Film molecular still maintained at a jacket temperature of 100° C. and 3-4mm. pressure for a period of about 1.5 hours. Typically, the refined residue product is a colorless liquid; and no infrared evidence for the unreacted triphosphite reactant was found, Example 2 being an exception.

The results are set forth in Table I:

TABLE I

| Example<br>Reaction Conditions | 1 | 2 | 3 | 4 | 5 | 6 | 7 | 8 |
|---|---|---|---|---|---|---|---|---|
| Triphosphite, gms.<br>(Moles) [a] | 408.8(0.4) | 408.8(0.4) | 511(0.5) | 511g(0.5) | 511 (0.5) | 2555(2.5) | 2555(2.5) | 2555(2.5) |
| Paraformaldehyde,gms.<br>(Moles) | 69.6(2.4) | 37.7(1.3) | 58(2.0) | 69.62g<br>(2.4) | 69.62g<br>(2.4) | 377 (13) | 377 (13) | 377 (13) |
| Moles HCHO/Phosphorus<br>atom equiv. | 2 | 1.08 | 1.33 | 1.60 | 1.60 | 1.74 | 1.74 | 1.74 |
| Reaction Temp., ° C. | 100 | 100 | 100 | 100 | 100–110 | 100 | 100 | 100 |
| Reaction Time, hrs. | 7 | 2.5 | 2.5 | 2.5 | 3.5 | 3.5 | 3.5 | 3.5 |
| Yield, Residue, gms. | 403.5 | 383 | 502 | 480 | 406 | Unrefined | Unrefined | Unrefined |
| Distillate, gms. | 16.5 | 13.40 | 13.20 | 15.62 | 10.70 | | | |
| Cold Traps, gms. | 13.7 | 7.8 | 11.0 | 12.70 | 10.8 | | | |
| Product Properties | | | | | | | | |
| Hydroxyl No., mg KOH/g,[b] | 249 | 267 | 305.9 | 315 | 325 | 325 | 354 | 351 |
| Refractive Index | 1.4690<br>at 25° C. | 1.4699<br>at 25° C. | 1.4691<br>at 20° C. | 1.4691<br>at 20° C. | 1.4691<br>at 20° C. | — | — | — |

TABLE I-continued

| Example Reaction Conditions | 1 | 2 | 3 | 4 | 5 | 6 | 7 | 8 |
|---|---|---|---|---|---|---|---|---|
| Viscosity, cps. at 25° C | 16,100 | 4,890 | 5,250 | 8,920 | 9,200 | 3,200 | 5,100 | 5,000 |
| Acid No., mg. KOH/g. | 7.81 | Nil | Nil | Nil | Nil | Nil | 0.056 | 0.239 |
| Elemental Analysis, % | | | | | | | | |
| Carbon | 47.20 | 48.30 | 47.50 | 47.40 | 47.00 | 47.90 | — | — |
| Hydrogen | 8.21 | 8.47 | 8.42 | 8.45 | 8.24 | 8.37 | — | — |
| Phosphorus | 8.29 | 8.59 | — | — | — | — | — | — |
| $P^{31}$ nmr Analysis Chemical Shifts, ppm from ext. $H_3PO_4$ | −24.70 | −138.40 −23.9 | — | — | — | — | — | — |
| Relative % of Chemical Shifts | 100 | 35/65 | — | — | — | — | — | — |

(a)The triphosphite used in these experiments had the following properties: OH No., 276, Acid No., Nil: P,9.1%, ref. index, 1.4645; viscosity, 1340 cps.; and $P^{31}$ nmr, −138.0, −22.4, and +6.6ppm.
(b)By the phenylisocyanate method.

As can be seen from Example 2, by nmr analysis, about 35% of the heptakis (dipropylene glycol) triphosphite reactant was unreacted. Increasing the ratio of moles HCHO/phosphorus atom equivalent to 2 (see Example 1) resulted in a reaction product having all of the phosphorus present as a phosphonate.

EXAMPLES 9–12

The novel polymethylol polyphosphonate formed in Example 7 was evaluated in a rigid urethane foam formulation to demonstrate its effectiveness as a flame retardant. A control (Example 12) was employed, and comparisons were made with two commercially available flame retardants.

The foam formulations, and the bench mix data are set forth in Table II:

TABLE II

| Formulations, parts by weight | | | | |
|---|---|---|---|---|
| Example | 9 | 10 | 11 | 12 |
| Resin: | | | | |
| Polyol A | 95 | 95 | 95 | 100 |
| Flame Retardant A | 5 | — | — | — |
| Flame Retardant B | — | 5 | — | — |
| Reaction Product of Example 7 | — | — | 5 | — |
| Water | 0.8 | 0.8 | 0.8 | 0.8 |
| Blowing Agent B | 28 | 28 | 28 | 28 |
| Surfactant A | 1 | 1 | 1 | 1 |
| N,N-dimethylethanolamine | 1 | 1 | 1 | 1 |
| Resin/NCO(1)Mix Ratio | 100/85 | 100/85 | 100/85 | 100/85 |
| Isocyanate Index, approximate | 110 | 112 | 111 | — |
| Resin/NCO Mix Temperatures, ° F. | 70/70 | 70/70 | 70/70 | 70/70 |
| Bench Mix Data:(2) | | | | |
| Mix Times, seconds | 30 | 30 | 30 | 30 |
| Cream Time, seconds | 35 | 35–40 | 30 | 35 |
| Gel Time, seconds | 125 | 130 | 125 | 125 |
| Rise Time, seconds | 205 | 225 | 210 | 200 |
| Free-Blow Density, pcf | 1.86 | 1.92 | 1.9 | 1.88 |
| Surface Friable | Slight | Slight | Slight | — |

(1)Commercially available polymeric isocyanate having a hydroxyl functionality of about 2.3.
(2)Foamable mixture hand mixed and poured into 12" × 12" × 12" open-top cardboard boxes.

The physical properties of the resulting foams were measured in the core of the 12-inch cube specimens, and the results are set forth in Table III:

TABLE III

| Example | 9 | 10 | 11 | 12 |
|---|---|---|---|---|
| Core Density, pcf | 1.81 | 1.90 | 1.83 | 1.87 |
| Closed Cells, pct | 91.0 | 90.5 | 89.4 | 90.60 |
| Compressive Strength | | | | |
| 25° C., psi, Parallel | 25.5 | 34.7 | 34.4 | 34.8 |
| Perpendicular | 14.1 | 12.9 | 10.3 | 11.0 |
| Cold Aging, pct Change | | | | |
| Weight, 14 days | −1.1 | −0.6 | −1.0 | — |
| Volume, 2 days | 0.7 | 0 | 0 | +1.4 |
| 14 days | −0.5 | −0.3 | −0.2 | +1.9 |
| Dry Aging, pct Change | | | | |
| Weight, 14 days | 0.8 | 0.8 | 1.0 | — |
| Volume, 14 days | 2.8 | 2.5 | 4.8 | −0.1 |
| Humid Aging, pct Change | | | | |
| Weight, 2 days | 0.3 | 0 | 0.1 | — |
| 7 days | 0 | −0.2 | −0.3 | — |
| 14 days | −0.6 | −0.5 | −0.9 | — |
| 28 days | −1.7 | −1.5 | −1.9 | — |
| Volume, 2 days | 6.1 | 5.6 | 8.2 | +0.06 |
| 7 days | 10.5 | 10.0 | 10.0 | +13.3 |
| 14 days | 12.6 | 12.0 | 13.5 | +14.9 |
| 28 days | 14.9 | 14.1 | 13.6 | — |
| Flammability, Rating | SE(a) | SE | SE | B(b) |
| Extinguishment Time, secs., Avg. | 27.4 | 41.6 | 54.6 | — |
| Burning Extent, ins., Avg. | 1.7 | 2.5 | 3.2 | — |
| Burning Rate, ins./min.,Avg. | 3.73 | 3.63 | 3.31 | 6.21 |

(a)Self-extinguishing
(b)Burned

As can be seen from the flammability testing, the polymethylol polyphosphonates of the present invention, while somewhat less effective than the other flame retardants employed, imparted satisfactory flame resistance to the resulting rigid foam.

EXAMPLES 13–17

The polymethylol polyphosphonates of Example 8 were incorporated into phenolic foam formulations in varying amounts.

The foam formulations, bench mix data and physical properties of the resulting foam products are described in Table IV:

TABLE IV

| Ingredient | Parts by Weight | | | | |
|---|---|---|---|---|---|
| Example | 13 | 14 | 15 | 16 | 17 |
| Phenolic Resin | 100 | 100 | 100 | 100 | 100 |
| Polyphosphonate of Example 8 | — | 5 | 10 | 15 | 20 |
| Surfactant B | 1.0 | 1.0 | 1.0 | 1.0 | 1.0 |
| Blowing agent A | 13 | 13 | 13 | 13 | 13 |
| Fluoboric Acid (48% aqueous) | 8.0 | 8.0 | 8.0 | 8.0 | 8.0 |
| Cream time, sec. | 60 | 65 | 70 | 80 | 90 |
| Rise time, sec | 135 | 205 | 235 | 270 | 320 |
| Density, pcf. | 2.14 | 1.81 | 1.87 | 1.90 | 1.93 |
| Closed cells, % | 00 | 00 | 00 | 00 | 00 |
| Compressive Strength | | | | | |
| 25° C., psi., Parallel | 24.5 | 18.9 | 17.0 | 17.0 | 15.1 |
| Perpendicular | 13.4 | 12.5 | 11.6 | 10.8 | 11.6 |
| Friability Resistance | | | | | |
| Weight Loss, %, 2 min. | 11 | 8 | 10 | 10 | 9 |
| 10 min. | 59 | 55 | 53 | 54 | 43 |
| The 10 min. friability weight loss normalized to 2.00 pcf. density | 63.1 | 45.5 | 49.5 | 51.3 | 41.5 |

As can be seen, the incorporation of the polymethylol polyphosphantes improved the friability resistance of the resulting foams.

EXAMPLES 18-19

Further polymethylol polyphosphonates according to the present invention were made by reacting tris(dipropylene glycol) phosphite and paraformaldehyde. The apparatus described in connection with Examples 1-8, as well as the general procedure, was utilized.

The reaction conditions and the resulting properties of the products formed are set forth in Table V:

| Example | 18 | 19 |
| --- | --- | --- |
| Reactions Conditions | | |
| Triphosphite gms. (Moles[a] | 430 (1) | 2150 (5.0) |
| Paraformaldehyde, gms. (Moles) | 46.4 (1.61) | 232 (8.0) |
| Reaction Temp., ° C. | 100 | 100 |
| Reaction Time, hrs. | 2.75 | 3.0 |
| Yield, Residue, gms. | 430 | 290 |
| Distillate, gms. | 15.7 | 68.2 |
| Cold Traps, gms. | 10.3 | 48.9 |
| Product Properties | | |
| Hydroxyl No., mg KOH/g.[b] | 453 | 389 |
| Viscosity, cps. at 25° C. | 1,525 | 1,650 |
| Acid No., mg. KOH/g. | 0.444 | 0.055 |
| Elemental Analysis, % | | |
| Carbon | 47.20 | 47.60 |
| Hydrogen | 8.65 | 8.52 |
| Phosphorus | 7.05 | 7.08 |
| P$^{31}$ nmr Analysis | | |
| Chemical Shifts, ppm from ext. H$_3$PO | — | −23.89[c] |
| Relative % of Chemical Shifts | — | 100 |

[a] the tris(dipropylene glycol) phosphite used in these experiments analyzed as follows: hydroxyl number, 395 mg. KOH/g.; acid number, 0.107 mg. KOH/g.; C, 45.34; H, 8.49; P, 9.00.
[b] Determined by the phenyl isocyanate method.
[c] The chemical shift at −23.89 is attributable to phosphonate phosphorus. Shifts for phosphite

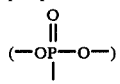

were not present.

What is claimed is:

1. Polymethylol polyphosphonates comprising the reaction product of formaldehyde and a trisubstituted phosphite selected from the group consisting of heptakis (dipropylene glycol) triphosphite; tris(dipropylene glycol) phosphite; diisodecyl pentaerythritol diphosphite; distearyl pentaerythritol diphosphite; bis(neopentylglycol)1,4-cyclohexanedimethylene phosphite; dineodyl pentaerythritol diphosphite; bis neopentylglycol triethyleneglycol diphosphite; diphenylpentaerythritol diphosphite; tetra(diphenylphosphite) pentaerythritol; tetrakis(nonylphenyl) polypropyleneglycol diphosphite; a polyphosphite characterized by the following repeating units:

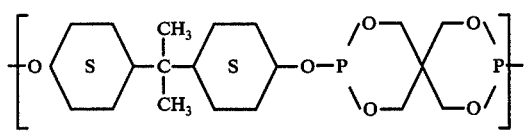

a polyphosphite characterized by the following repeating units:

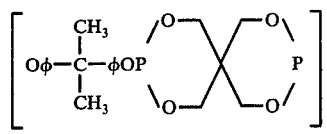

and mixtures thereof, the reaction being carried out in the presence of a polyol as a protic solvent when the trisubstituted phosphite does not contain polyhydroxyl functionality.

2. The polymethylol polyphosphonates of claim 1 wherein the trisubstituted phosphite is heptakis (dipropylene glycol) triphosphite.

3. The polymethylol polyphosphonates of claim 1 wherein the trisubstituted phosphite is tris(dipropylene glycol) phosphite.

4. A process for producing polymethylol polyphosphonates which comprises reacting formaldehyde with a trisubstituted phosphite selected from the group consisting of heptakis (dipropylene glycol) triphosphite; tris (dipropylene glycol) phosphite; diisodecyl pentaerythritol diphosphite; distearyl pentaerythritol diphosphite; bis (neopentylglycol)1,4-cyclohexanedimethylene phosphite; dineodyl pentaerythritol diphosphite; bis neopentylglycol triethyleneglycol diphosphite; diphenylpentaerythritol diphosphite; tetra (diphenylphosphite) pentaerylthritol tetrakis (nonylphenyl) polypropyleneglycol diphosphite; a polyphosphite characterized by the following repeating units:

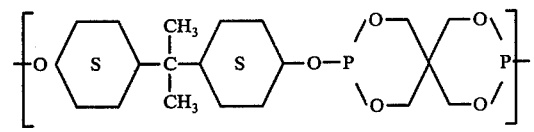

a polyphosphite characterized by the following repeating units:

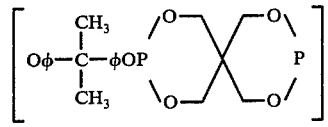

and mixtures thereof, the reaction being carried out in the presence of a polyol as a protic solvent when the trisubstituted phosphite does not contain polyhydroxyl functionality.

5. The process of claim 4 wherein the reaction is carried out at a temperature in the range of from about 25° to about 110° C.

6. The process of claim 4 wherein the mole ratio of formaldehyde to the trisubstituted phosphite is from about 1:1 to about 6:1.

7. The process of claim 4 wherein the ratio of the moles of formaldehyde to the atoms of phosphorus present in the trisubstituted phosphite is from about 1:1 to about 2:1.

8. The process of claim 4 wherein the polyol is present in an amount sufficient to introduce at least two hydroxyl groups per molecule of the trisubstituted phosphite.

9. The process of claim 4 wherein the trisubstituted phosphite is heptakis (dipropylene glycol) triphosphite.

10. The process of claim 4 wherein the trisubstituted phosphite is tris(dipropylene glycol) phosphite.

* * * * *